United States Patent [19]

Sibner

[11] Patent Number: 5,766,011
[45] Date of Patent: Jun. 16, 1998

[54] DENTAL BLEACHING COMPOSITION AND METHOD

[76] Inventor: Jeffrey A. Sibner, 352 Tall Meadow La., Yardley, Pa. 19067

[21] Appl. No.: 757,248

[22] Filed: Nov. 27, 1996

[51] Int. Cl.⁶ ..................... A61C 5/00
[52] U.S. Cl. ..................... 433/215
[58] Field of Search ............ 433/215, 216; 424/53, 52; 106/35

[56] References Cited

U.S. PATENT DOCUMENTS

| | | |
|---|---|---|
| 4,582,701 | 4/1986 | Piechota . |
| 4,661,070 | 4/1987 | Friedman ............ 433/203.1 |
| 4,687,663 | 8/1987 | Schaeffer . |
| 4,877,401 | 10/1989 | Higuchi et al. . |
| 4,983,380 | 1/1991 | Yarborough . |
| 4,983,381 | 1/1991 | Torres Zaragoza ............ 424/53 |
| 5,009,885 | 4/1991 | Yarborough . |
| 5,032,178 | 7/1991 | Cornell ............ 106/35 |
| 5,041,280 | 8/1991 | Smigel . |
| 5,123,845 | 6/1992 | Vassiliadis et al. . |
| 5,240,415 | 8/1993 | Haynie ............ 433/216 |
| 5,275,564 | 1/1994 | Vassiliadis et al. ............ 433/226 |
| 5,306,143 | 4/1994 | Levy . |
| 5,318,562 | 6/1994 | Levy et al. . |
| 5,324,200 | 6/1994 | Vassiliadis et al. ............ 433/224 |
| 5,409,631 | 4/1995 | Fisher . |
| 5,501,599 | 3/1996 | Rechmann ............ 433/215 |
| 5,645,428 | 7/1997 | Yarborough ............ 433/215 |

*Primary Examiner*—Cary E. O'Connor
*Attorney, Agent, or Firm*—Karen Lee Orzechowski; Nath & Associates

[57] ABSTRACT

A dental bleaching composition having enhanced effectiveness and reduced sensitivity, its method of use, and a kit containing the ingredients for making the composition. The dental bleaching composition comprises hydrogen peroxide, an inert silica compound, sodium hydroxide, and a discrete inert particulate pigmented material in the form of a gel with a pH of about 9.5 to 10. The dental bleaching composition is placed on the teeth to be bleached, exposed to argon laser energy, and removed. The process is then repeated for a number of cycles. Neutral sodium fluoride is then applied to the bleached teeth for at least 10 minutes to reduce or eliminate post-bleaching sensitivity.

21 Claims, No Drawings

1

DENTAL BLEACHING COMPOSITION AND METHOD

FIELD OF THE INVENTION

The present invention relates to dental bleaching compositions and methods, and more particularly to dental bleaching compositions and methods utilizing a laser to enhance the bleaching action. The invention more particularly relates to dental bleaching compositions and methods with enhanced removal of both extrinsic and intrinsic discolorants from the dentition and with reduced pain or sensitivity associated with the bleaching process.

BACKGROUND OF THE INVENTION

Discolorations of the dentition are traditionally classified into two main categories, extrinsic and intrinsic. Extrinsic discolorations, or stains, are on the outer surface of the dentition and can be removed from the surface by dental instruments or polishing abrasives. Intrinsic discolorations, or stains, located within the crystalline matrix of the enamel and dentin and cannot be removed by the use of dental instruments or polishing abrasives.

Extrinsic discolorations or stains are usually superficial stains of the tooth surface resulting from the deposition of a film, pigments or calculus on the teeth. Many agents can cause such extrinsic discolorations including common substances such as coffee, tea, artificial food colorations, grapes, berries, smoking or chewing of tobacco, and the like. Stain intensity, and consequently ease of removal of the stains, are worsened by the penetration of the stain into tooth surface irregularities such as pits, cracks, grooves, exposed dentin, and bared root surfaces resulting from recession. The degree of difficulty of removal of the stain increases the deeper the penetration of the stain, with some stains penetrating to such a depth that the removal is extremely difficult or virtually impossible using current methods of stain removal.

Intrinsic discolorations can have many causes of either an endogenous or exogenous origin and may occur during or after odontogenesis. During the process of creation of the teeth, referred to as odontogenesis, the teeth may become discolored from changes in the quality or quantity of enamel or dentin, or from incorporation of discoloring agents in the hard tissues, and may be caused by many diseases and medications, such as tetracycline. Post-eruption discolorations occur when discoloring agents enter the dental hard tissues from either the pulp cavity or tooth surface and can be caused by trauma, aging, metals, dental materials, and contact with or ingestion of certain foods and beverages.

A commonly practiced technique for removing discoloration is the practice of external bleaching, often with hydrogen peroxide. However, known bleaching agents are able only to remove discoloring agents located within five to seven microns from the enamel surface due to the high inorganic content and limited permeability of the enamel. Thus intrinsic discolorations and deeply penetrating extrinsic discolorations are left untouched.

Many attempts have been made over the years to find a bleaching system capable of removing intrinsic and deeply penetrating extrinsic stains. Chemical reagents that have been tried include hydrogen peroxide, oxalic acid, pyrozone (hydrogen peroxide and ethyl ether), muriatic acid, and chlorine compositions, as well as bleaching agents such as a 30% superoxol (30% hydrogen peroxide stabilized by reducing the pH to 4.0–5.0) or a pyrozone (30% hydrogen peroxide and ethyl ether) used in conjunction with heat from a light source, such as a tungsten lamp, or a heated instrument or bleaching paddle. The addition of heat to accelerate hydrogen peroxide's bleaching action has made such systems capable of reacting fast enough for in-office use. However, side effects due to the increased reactivity can be quite painful and include inflamed or burned gingiva and lips, as well as significant post-bleaching tooth sensitivity.

Recently, in an effort to overcome these side effects, "cold bleaching" systems were developed. These systems used longer room temperature reaction times instead of shorter heat activated reaction times. In these cold bleaching systems, the hydrogen peroxide is thickened or gelled to allow the hydrogen peroxide to form a coating capable of remaining in contact with the teeth for extended period of time. Although the cold bleaching systems eliminated the side effects of the application of heat, a number of office visits were still required to achieve satisfactory results and post-bleaching sensitivity still occurred.

SUMMARY OF THE INVENTION

It has now been discovered that the dental bleaching composition of the present invention can be used in conjunction with a laser to provide enhanced effectiveness of the bleaching action while reducing post-bleaching sensitivity.

The dental bleaching composition comprises hydrogen peroxide, an inert silica gelling compound, sodium hydroxide, and a discrete inert particulate pigmented laser enhancing material. These materials are admixed to form a gel with a pH of about 9.5 to about 10. The discrete particles are preferably in a complementary color to the color of the laser and are dispersed throughout the bleaching composition so that the laser beam can pass through to the surface of the tooth while the particles act to increase the absorption of the laser thus increasing the effectiveness of the bleaching composition.

The dental bleaching composition is placed on the tooth surfaces to be bleached, the coated tooth surfaces are exposed to argon laser energy, and then the coating is removed from the tooth surfaces, preferably by rinsing. The process is then repeated for a number of cycles. Neutral sodium fluoride is then applied to the bleached teeth for at least 10 minutes to reduce or eliminate post-bleaching sensitivity.

A kit containing the ingredients allows single dose applications to be mixed immediately before use.

DETAILED DESCRIPTION OF THE INVENTION

The present invention is directed to a novel dental bleaching composition and its method of use which results in enhanced bleaching action while reducing or eliminating post-bleaching sensitivity. The topical dental bleaching composition of the present invention comprises a gel formed from admixing hydrogen peroxide with an inert silica gelling compound. The pH of the gel is modified or adjusted at least 9.0 to reduce post-bleeding sensitivity. To enhance the effectiveness of the bleaching composition, discrete inert laser enhancing particles are dispersed throughout the composition.

The hydrogen peroxide is present in concentrations ranging from about 5% to about 70% by volume, and more preferably from about 35% to about 60% by volume. The amount of hydrogen peroxide present is about 90 to 95% by volume of the total mixture.

Any suitable inert silica compound can be used that is capable of forming a gel or thickened mixture when admixed with the hydrogen peroxide. Suitable silica compounds include silicon dioxide, fumed silica and the like. Preferably the silica compound is in a finely divided form that enhances the gelling reaction with the hydrogen peroxide. The preferred concentration of the silica gelling agent is approximately 5 to 10% by volume.

Hydrogen peroxide is a concentration-dependant pulpal irritant. The higher the concentration of hydrogen peroxide placed on the surface of a tooth, the more rapidly the concentration of hydrogen peroxide rises within the enamel and dentin of the tooth. Even at lower concentrations, hydrogen peroxide can irritate the pulp causing pulpitis and at higher concentrations, can cause pulpal death.

One embodiment of the present invention is directed to the discovery that even with very high concentrations of hydrogen peroxide, post-bleaching tooth and dental sensitivity can be significantly decreased by maintaining hydration of the dental tissues during the bleaching process and thus eliminating pulpitis and its attendant sensitivity. It has been discovered that there is a significant difference in pain both during and after bleaching teeth with a hydrogen peroxide/silicon dioxide gel and an argon laser when the teeth were rinsed with water every 3 to 5 minutes during the bleaching procedure to keep them hydrated. In these tests, patients had a hydrogen peroxide and silicon dioxide gel placed on six maxillary anterior teeth, canine to canine. The teeth were exposed, in turn, to 40 seconds of argon laser light per tooth.

On three teeth, the bleaching gel was wiped away with a cotton gauze and on the other three teeth, the bleaching gel was rinsed away and the teeth were bathed in water for approximately 20 seconds. The bleaching gel was then replaced and the cycle was repeated for a total of six cycles. Patients reported significantly less pain during and after the bleaching procedure on the teeth that were hydrated. When the sides were switched and the teeth that had been bathed in water were wiped clean instead, while the teeth that were wiped were hydrated, the patients reported that the teeth that were sensitive had switched as well.

It has unexpectedly been discovered that adjusting or modifying the pH of the bleaching composition to at least 9.0, and more preferably between 9.5 and 10.0 results in a significant reduction in post-bleaching sensitivity. Any suitable pH modifier can be used. In one embodiment of the present invention, sodium hydroxide (NaOH) is used to adjust the pH.

In a preferred embodiment of the present invention, an argon laser light is used to enhance the bleaching action of the dental bleaching composition of the present invention. Theoretically, argon laser light enhances the speed by which enamel and dentin can be bleached by any or all of the following mechanisms: i) lowering the energy needed to break down the stain molecules within the teeth, ii) pushing the bleaching gel into the tooth more rapidly, and iii) interacting with the bleaching gel to enhance its reactivity. It has been discovered that teeth coated with a hydrogen peroxide and fumed silica gel and exposed to argon laser light bleach lighter than teeth of the same shade bleached with the gel alone. This effect is dependent on the strength of the argon laser, with a laser yielding an energy density of 600–800 milliwatts/cm$^2$ bleaching the coated tooth surfaces more effectively than a laser yielding an energy density of 400–600 milliwatts/cm$^2$ but at the cost of increased sensitivity during and following the bleaching process. This may be due to one or both of the following mechanisms. i) The laser energy "pushes" the hydrogen peroxide into the tooth more rapidly —the concentration of hydrogen peroxide at any distance from the surface of the tooth may be greater when the tooth is bathed in argon laser light than in the absence of the laser. ii) The laser energy may contribute directly to pulpal irritation.

In a preferred embodiment of the present invention, the bleaching action of the dental bleaching composition is enhanced by the inclusion of a discrete inert colored particulate material into the bleaching composition. The discrete inert colored particulate matter is preferably a color complement to the laser light. For example, an argon laser utilizes a blue light. Therefore, an orange particulate material would be preferred since orange is the color complement to blue.

There are no studies that show hydrogen peroxide is activated or made more reactive directly by exposure to argon laser energy. However, it has been discovered that the inclusion of an inert orange compound formed into 100–200 micron particles makes hydrogen peroxide more reactive when exposed to an intense blue light, i.e. an argon laser. As discussed above, orange is the color complement to blue, and as such, absorbs the energy of the blue argon laser light in an efficient manner allowing it to be retransmitted as thermal energy. In the micro-environment surrounding the orange particles, this increase in thermal energy makes the hydrogen peroxide more reactive.

The discrete inert colored particulate material can be made of any suitable material that will not react with the hydrogen peroxide and that will not leach its color into the tooth surface during the bleaching process. Suitable materials include colored or coated porcelain, ceramic, thermoplastic or polymeric resins such as acrylic resins, cellulosic resins, ceramic fiber compounds, fluoroplastic resins, polyamide resins, polycarbonate resins, phenolic resins, polyethelene resins, polyester resins, polymethylpentene resins, polyoxymethylene resins, polyphenylene resins, polypropylene resins, polystryrene resins, polyvinyl resins, nitrile resins, terephthalic resins, or glass fiber compounds. However, other types of plastics and polymeric materials known to those in the art may be used provided that they do not react. The particles can be coated or colored by any suitable means and such coating and coloring processes are well known in the art.

The size of the particles can vary and preferably range from about 50 microns to about 350 microns, and more preferably from about 100 microns to about 200 microns.

The amount or density of the particles in the bleaching gel is sufficient to allow the laser to enhance the reactivity of the hydrogen peroxide. However, the particulate density or amount is not so great that it blocks the laser light from reaching the surface of the tooth.

In another embodiment of the present invention, post-bleaching sensitivity is further reduced by the application of neutral sodium fluoride to the bleached teeth for at least ten minutes. Fluoride has been used in dentistry to reduce sensitivity for many years. Often, when the root surface of teeth are exposed to the oral cavity due to gingival recession, these teeth become sensitive to hot, cold and sometimes sweets. Fluoride has been shown to reduce this sensitivity by combining with the crystalline structure of the tooth to form fluorapatite and by blocking dentinal tubuals. It has been discovered that the application of neutral sodium fluoride for at least ten minutes following bleaching teeth with a gel of 50% hydrogen peroxide, fumed silica and sodium hydroxide, in conjunction with exposure to an argon laser, significantly reduces or eliminates the intense pain that other wise results. This post bleaching pain usually has an onset of about 2 hours post-bleaching and lasts for 2 or more days. When neutral sodium fluoride is applied to the teeth for 5 minutes post bleaching, the pain level is often diminished and lasts for only 8 to 12 hours. When neutral sodium fluoride is applied to the bleached teeth for a full 10 minutes after bleaching is completed, post-bleaching sensitivity is almost completely eliminated.

The dental bleaching composition of the present invention can be supplied to dental practitioners in the form of a kit containing ingredients sufficient for either individual or multiple treatments. The ingredients can be supplied individually in separate containers or vials, or can have multiple ingredients premixed so that the hydrogen peroxide containing mixture can be admixed by the dental professional with the silicon compound at the point of use. In one embodiment, it is contemplated that the dental professional will be supplied with a kit containing 2 premeasured vials, one containing hydrogen peroxide and the other containing sodium hydroxide, and a jar containing a premixed quantity of the inert silica and orange compounds. All items are packaged with a protocol by which safe and effective use of the materials can be achieved.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed:

1. A method for bleaching teeth comprising the steps of:
   forming a bleaching gel by admixing hydrogen peroxide with a thickening agent, a pH modifier and discrete inert laser enhancing particles;
   applying said bleaching gel to the surface of the teeth to be bleached;
   exposing the bleaching gel coated tooth surface to a laser;
   removing the bleaching gel from the tooth surface.

2. The method of claim 1 wherein the process is repeated until the desired degree of bleaching of the teeth is reached.

3. The method of claim 2 further comprising the step of applying sodium fluoride to the bleached teeth for at least 10 minutes.

4. The method of claim 1 wherein said discrete inert laser enhancing particles are complementary in color to the color of said laser.

5. The method of claim 4 wherein said particles have a size from about 100 to 200 microns.

6. The method of claim 4 wherein said laser is an argon laser and said particles are orange.

7. The method of claim 6 wherein said particles are crushed glass beads having a diameter from about 100 to 200 microns.

8. The method of claim 6 wherein said particles are orange color coated beads having a diameter from about 100 to 200 microns.

9. The method of claim 1 wherein said particles are present in an amount sufficient to enhance the activity of the hydrogen peroxide.

10. The method of claim 1 wherein said particles are present in an amount such that light from the laser can penetrate the bleaching composition to reach the surface of the tooth.

11. The method of claim 1 wherein said hydrogen peroxide has a concentration from about 5% to about 70% by volume.

12. The method of claim 11 wherein said hydrogen peroxide has a concentration from about 35% to about 60% by volume.

13. The method of claim 1 wherein the pH is from about 9.5 to about 10.0.

14. The method of claim 13 wherein the pH modifier is sodium hydroxide.

15. The method of claim 1 wherein the laser is an argon laser.

16. The method of claim 15 wherein the energy density of said argon laser is from about 400 milliwatts/cm$^2$ to about 800 milliwatts/cm$^2$.

17. The method of claim 16 wherein tooth sensitivity is further reduce by using an energy density of about 400 milliwatts/cm$^2$.

18. The method of claim 16 wherein reactivity of the hydrogen peroxide is increase by using an energy density of about 600 milliwatts/cm$^2$ to about 800 milliwatts/cm$^2$.

19. The method of claim 1 with further reduced tooth sensitivity, said method further comprising the step of hydrating the tooth surface and surrounding dental tissue by rinsing the tooth surface following or during the step of removing the bleaching gel from the tooth surface.

20. A method for enhancing the reactivity of a hydrogen peroxide containing dental bleaching composition comprising the steps of:
   mixing discrete inert laser enhancing particles with said hydrogen peroxide containing dental bleaching composition to form a laser enhanced bleaching mixture;
   coating the tooth surface to be bleached with said mixture;
   exposing said coated tooth surface to laser light; and
   removing said mixture from said tooth surface.

21. A method for decreasing sensitivity during dental bleaching, said method comprising the steps of:
   forming a dental bleaching composition;
   modifying the pH of said dental bleaching composition to about 9.5 to about 10.0;
   applying said pH modified dental bleaching composition to the surface of the teeth;
   allowing the bleaching composition to react with the surface of the teeth to bleach the teeth;
   removing said reacted bleaching composition from the surface of the teeth;
   hydrating the surface of the teeth and the surrounding dental tissue; and
   applying sodium fluoride to the surface of the teeth for at least 10 minutes.

* * * * *